US009766167B2

(12) United States Patent
Paterlini-Brechot

(10) Patent No.: US 9,766,167 B2
(45) Date of Patent: Sep. 19, 2017

(54) PROCESS AND DEVICE FOR SEPARATING BIOLOGICAL PARTICLES CONTAINED IN A FLUID BY MEANS OF FILTRATION

(71) Applicants: INSTITUT NATIONAL DE LA SANTE ET DE LA RECHERCHE MEDICALE (INSERM), Paris (FR); ASSISTANCE PUBLIQUE-HOPITAUX DE PARIS, PARIS (FR); UNIVERSITE RENE DESCARTES—PARIS V, Paris (FR)

(72) Inventor: Patrizia Paterlini-Brechot, Paris (FR)

(73) Assignees: INSTITUT NATIONAL DE LA SANTE ET DE LA RECHERCHE MEDICALE (INSERM), Paris (FR); ASSISTANCE PUBLIQUE-HOPITAUX DE PARIS, Paris (FR); UNIVERSITE RENE DESCARTES-PARIS V, Paris (FR)

( * ) Notice: Subject to any disclaimer, the term of this patent is extended or adjusted under 35 U.S.C. 154(b) by 0 days.

(21) Appl. No.: 14/517,288

(22) Filed: Oct. 17, 2014

(65) Prior Publication Data

US 2015/0104791 A1    Apr. 16, 2015

Related U.S. Application Data

(63) Continuation of application No. 11/908,545, filed as application No. PCT/FR2006/000562 on Mar. 14, 2006, now abandoned.

(30) Foreign Application Priority Data

Mar. 24, 2005    (FR) ...................................... 05 02945

(51) Int. Cl.
*G01N 1/40*  (2006.01)
*B01L 3/00*  (2006.01)
*B01L 9/00*  (2006.01)

(52) U.S. Cl.
CPC ........ *G01N 1/4077* (2013.01); *B01L 3/50255* (2013.01); *B01L 9/523* (2013.01);
(Continued)

(58) Field of Classification Search
CPC ................................................. B01L 3/50255
See application file for complete search history.

(56) References Cited

U.S. PATENT DOCUMENTS 4,493,815 A * 1/1985 Fernwood .............. B01D 61/18
210/232
4,510,119 A * 4/1985 Hevey ................. B01L 3/50853
206/443

(Continued)

*Primary Examiner* — Peter Keyworth
(74) *Attorney, Agent, or Firm* — Oblon, McClelland, Maier & Neustadt, L.L.P.

(57) ABSTRACT

The invention relates to a method of separating biological particles from the liquid containing same for purification, analysis and optionally diagnostic purposes. The inventive method comprises at least one step involving vertical filtration through a filter having a porosity that is adapted to the type of biological particles to be separated, such that said particles are retained by the filter. The invention is characterized in that: (i) the method involves the use of a filter comprising at least one basic filtration zone, whereby each basic filtration zone has a limited surface area; and (ii) the surface area of each basic filtration zone and the number of basic filtration zones are selected as a function of the type of liquid to be filtered, the type of biological particles to be separated and the volume of liquid to be filtered.

18 Claims, 8 Drawing Sheets

(52) U.S. Cl.
CPC . *B01L 2200/0631* (2013.01); *B01L 2400/049* (2013.01); *G01N 2001/4088* (2013.01)

(56) References Cited

U.S. PATENT DOCUMENTS

| | | | | |
|---|---|---|---|---|
| 4,787,988 | A * | 11/1988 | Bertoncini | B01D 29/05 210/406 |
| 5,190,666 | A * | 3/1993 | Bisconte | B01D 29/05 210/143 |
| 5,624,815 | A * | 4/1997 | Grant | B01L 3/5025 210/405 |
| 6,805,840 | B1 * | 10/2004 | Tajima | B01L 3/0231 210/695 |
| 2004/0121471 | A1 * | 6/2004 | Dufresne | 436/45 |
| 2005/0049793 | A1 * | 3/2005 | Paterlini-Brechot | C12Q 1/6879 702/19 |

* cited by examiner

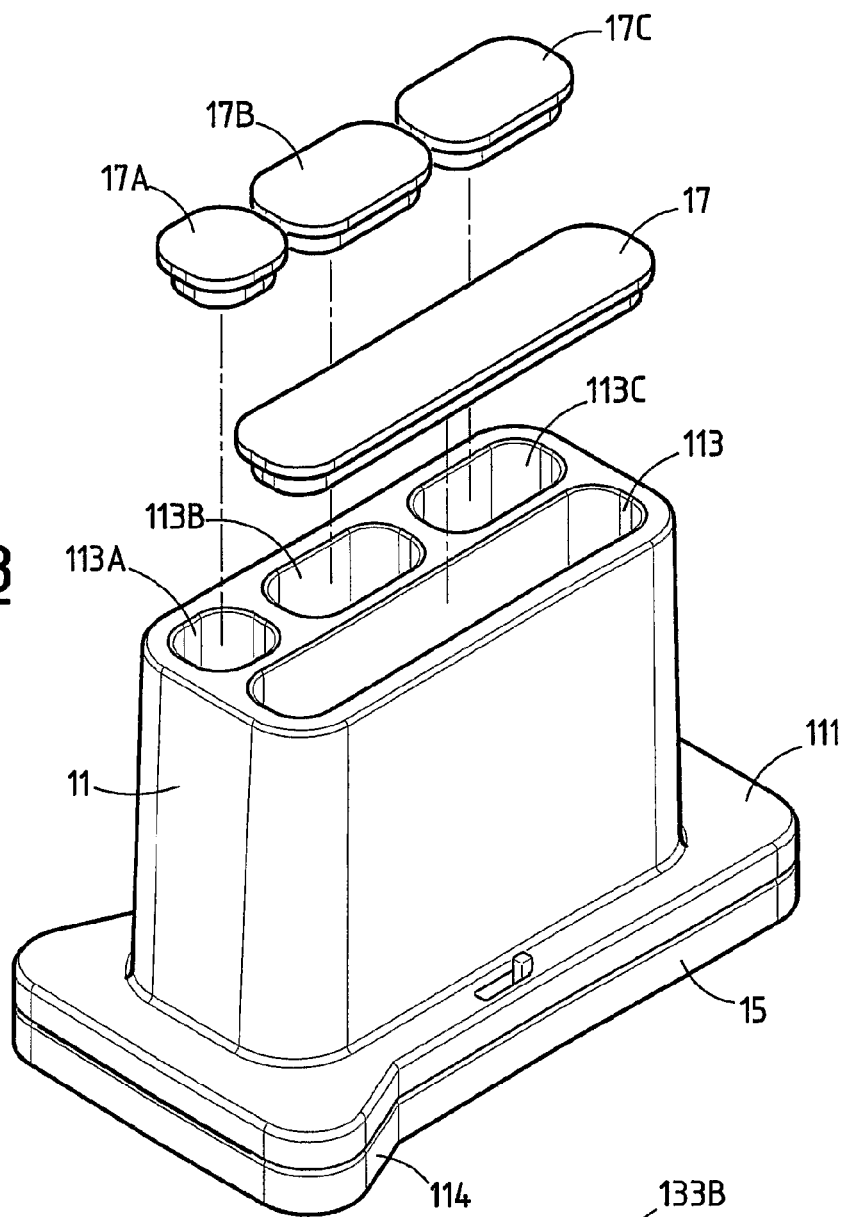
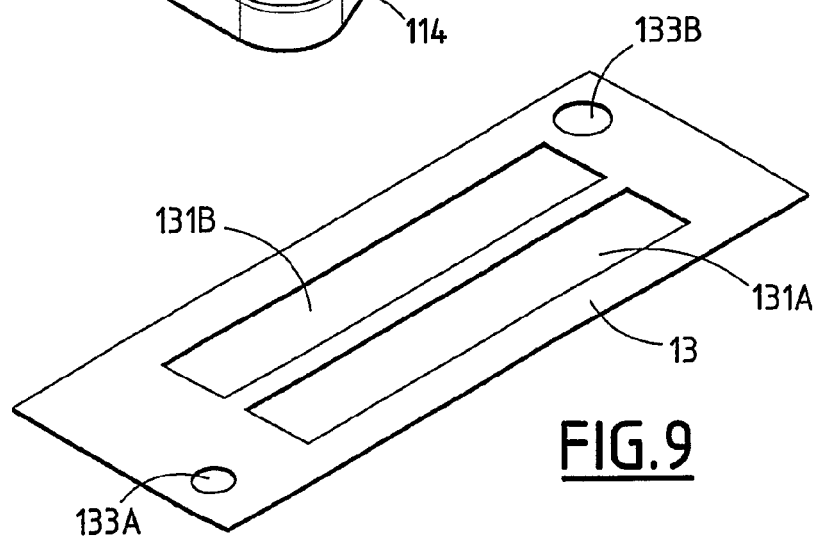

PROCESS AND DEVICE FOR SEPARATING BIOLOGICAL PARTICLES CONTAINED IN A FLUID BY MEANS OF FILTRATION

This application is a continuation of application Ser. No. 11/908,545, filed Sep. 13, 2007, which is the National Stage of International Application No. PCT/FR2006/000562, filed Mar. 14, 2006 (which is hereby incorporated by reference).

The present invention relates to the separation of biological particles contained in a fluid, which can be separated on the basis of their size, separation being carried out by vertical filtration using a filter suited to the nature of the particles to be isolated. The particles are isolated in particular for the purposes of purification or analysis and possibly for diagnosis.

To develop non-invasive diagnostic methods, particularly in the prenatal field, or early diagnosis methods, particularly in the field of oncology, it has been proposed in patent applications FR 2 782 730 and FR 2 824 144 to seek rare characteristic cells in biological fluids taken from patients. In these methods, the cells to be detected are searched for by means of an enrichment operation by filtration using in particular an ISET-type filtration machine such as the machine described in patent WO 91/11245. These methods consist of filtering a biological fluid, which may have undergone specific preparation, through a filter the pores or porosity of which are suitable, in such a way that the cells sought form on the filter a filtration residue, which is then analysed. The porosity of the filter, the preparation of the biological fluid and the analysis method are chosen according to the nature of the cells sought.

These methods were developed initially using a filtration appliance designed to search for particles in milk for quality control purposes. Although necessary adaptations were made, given the nature of the filtered fluids and the particles sought, these methods still have drawbacks. In particular, blood is difficult to filter.

In about 30% of cases, filtration of this fluid is interrupted by clogging, making it unusable.

In addition, the device used to contain the sample of fluid to be filtered comprises a mechanism to achieve a seal that is rather inconvenient to use.

Finally, and in general, filtration reliability sufficient for use experimentally in a laboratory is not sufficient for use for mass diagnostic purposes.

The object of the invention is to overcome this drawback by offering a means of making the operation of isolating by vertical filtration the cells contained in a fluid or more generally of separating biological particles from a fluid that contains them more reliable so as to make it suitable in particular for use for diagnostic purposes.

Accordingly, the invention relates to a process for separating biological particles and the fluid that contains them for the purposes of purification or analysis and possibly for diagnosis, comprising at least one vertical filtration stage through a filter the porosity of which is suited to the nature of the biological particles to be separated so that said biological particles are retained by the filter, characterised in that a filter is used comprising at least one elementary filtration area, each elementary filtration area having a limited surface, and in that the surface of each elementary filtration area and the number of elementary filtration areas is chosen according to the nature of the fluid to be filtered, the nature of the biological particles to be separated and the volume of fluid to be filtered.

Each elementary filtration area of said process has a surface equal to that of a disk with a diameter of between 0.6 cm and 3 cm, and the number of elementary filtration area is chosen so that the ratio of the volume of fluid filtered to the filtration surface is less than 40 ml/cm$^2$, and preferably greater than 0.14 ml/cm$^2$.

Preferably, each elementary filtration area has a surface equal to that of a disk with a diameter greater than or equal to 0.8 cm.

Preferably, the filter has pores calibrated to a size of between 3 μm and 100 μm and a pore density of between $3 \times 10^3$ and $5 \times 10^6$ pores/cm$^2$.

Preferably, filtration is carried out by a reduction in pressure of between 0.05 bar and 1 bar with, possibly, an increase in pressure of less than 1 bar.

To carry out filtration, it is preferable to use a filter forming a badge suitable to be associated with a means of analysing filtration residues by locating the elementary filtration areas.

Preferably, the badge forming the filter is incorporated in a single-use filtration module comprising at least one chamber for containing the fluid to be filtered, and that can be treated before use to sterilise it or to free it from enzymes that digest DNA, RNA or proteins.

The biological particles to be separated are, for example, cells. In this case, prior to filtering the fluid containing the cells, a sample of fluid for filtering may be prepared from a sample of fluid containing cells such as a biological fluid or cell culture by pre-enriching it with the cells to be separated and/or by diluting it.

The fluid containing the cells may be blood and, preferably, the filter in this case has calibrated pores of between 5 μm and 25 μm.

The biological particles may also be fibrins.

The fluid containing the biological particles is urine and the calibrated pores of the filter are between 8 μm and 100 μm.

The process can be used for the detection of cells for diagnostic purposes such as tumour, foetal, endothelial, fibroblastic, muscle, nerve or monocytal cells, cell strains, organ cells, precursors or haematopoietic cells, in a biological fluid such as blood, urine, ascites, cephalorachidian fluid, milk, pleural extravasation, fluid for washing the neck of the uterus, cell suspension fluid obtained by biopsy, by a surgical method or by mouth washing, or for the detection of animal or vegetable cells.

The invention also relates to a filtration module for implementing the process, said module comprising:
- a chamber block comprising at least one compartment closed at its lower portion by a base comprising at least one opening;
- a filter support drawer comprising at least one hole, each hole being arranged facing an opening in the chamber block;
- a filter gripped between the lower face of the chamber block and the support drawer.

In this module, the dimensions of each opening in the base of the chamber block and the dimensions of each hole in the filter support drawer are such that each pair made up of an opening in the base of the chamber block and the associated hole in the filter support draw, define an elementary filtration area of limited surface and in that the useful volume of each compartment is proportional to the number of elementary filtration areas situated in the base of the compartment.

Preferably, the surface of an elementary filtration area is equal to that of a disk with an equivalent diameter of between 0.6 cm and 3 cm, and the ratio of the useful volume of each compartment to the sum of the surfaces of the openings comprised in the base of the compartment is less than 40 ml/cm$^2$, and preferably greater than 0.14 ml/cm$^2$.

Preferably, the dimensions of at least one opening in the base of the chamber block and of a corresponding hole in the filter support drawer are such that the surface of the corresponding elementary filtration area is greater than or equal to that of a disk 0.8 cm in diameter.

Preferably, at least one compartment may be divided into part compartments by at least one removable separation wall, such that at least one part compartment comprises in its base at least one opening and that the ratio of the volume of said part compartment to the sum of the surfaces of the openings in the base of the part compartment is less than 40 ml/cm$^2$, and preferably greater than 0.14 ml/cm$^2$.

Preferably, the filtration module comprises a grooved sealing joint arranged between the base of the chamber block and the filter, comprising at least one hole corresponding to a hole in the base of the chamber block, the hole being surrounded by at least one projecting lip.

In addition, the filtration module preferably also comprises a plate joint between the filter and the filter support, comprising at least one opening opposite a hole in the filter support.

The filter may form a badge the central portion of which comprises at least one porous area and the periphery of which forms a frame comprising means for indexing its position on the filter support.

The indexation means are, for example, at least two holes of different diameter designed to cooperate with studs of corresponding diameter provided on the filter support.

Preferably, at least a central porous portion of the filter comprises between $3\times10^3$ and $5\times10^6$ pores per cm$^2$ of between 3 μm and 100 μm.

Preferably, the filtration module also comprises at least one stopper for closing the upper opening of a compartment.

Preferably, the chamber block comprises, at its lower portion, a rim extending outwards and cooperating with at least one assembly pin allowing the filter to be gripped between the filter support and the chamber block, the assembly pin comprising a breakable end extending above the rim of the chamber block.

Preferably, all its parts are made of materials suited to a sterilisation operation or designed to render them free from RNases, DNases or proteinases.

Finally, the invention relates to a filtration module support for retaining a filtration module on a filtration machine, comprising at least one cam that can move between an open position and a gripping position, designed to put pressure on the filter between the filter support and the chamber block.

Preferably, at least one cam is designed so that, if the filtration module comprises at least one fixing pin one end of which is breakable, the end of at least one fixing pin is cut when pressure is applied to the filter by at least one cam.

The support block forms part of a filtration machine.

Preferably, the filtration module also comprises a means designed to cooperate with a complementary means on a support block, so as to impose the orientation of the filtration module in relation to the support block, and the support block comprises a means designed to cooperate with a means on a filtration module, so as to index the orientation of the filtration module in relation to the support block.

The invention will now be described in more detail but in a non-limiting manner with regard to the accompanying drawings in which:

FIG. 8 is a perspective view of a filtration module according to a variant.

FIG. 9 is a perspective view of a badge-filter.

Figure 1:
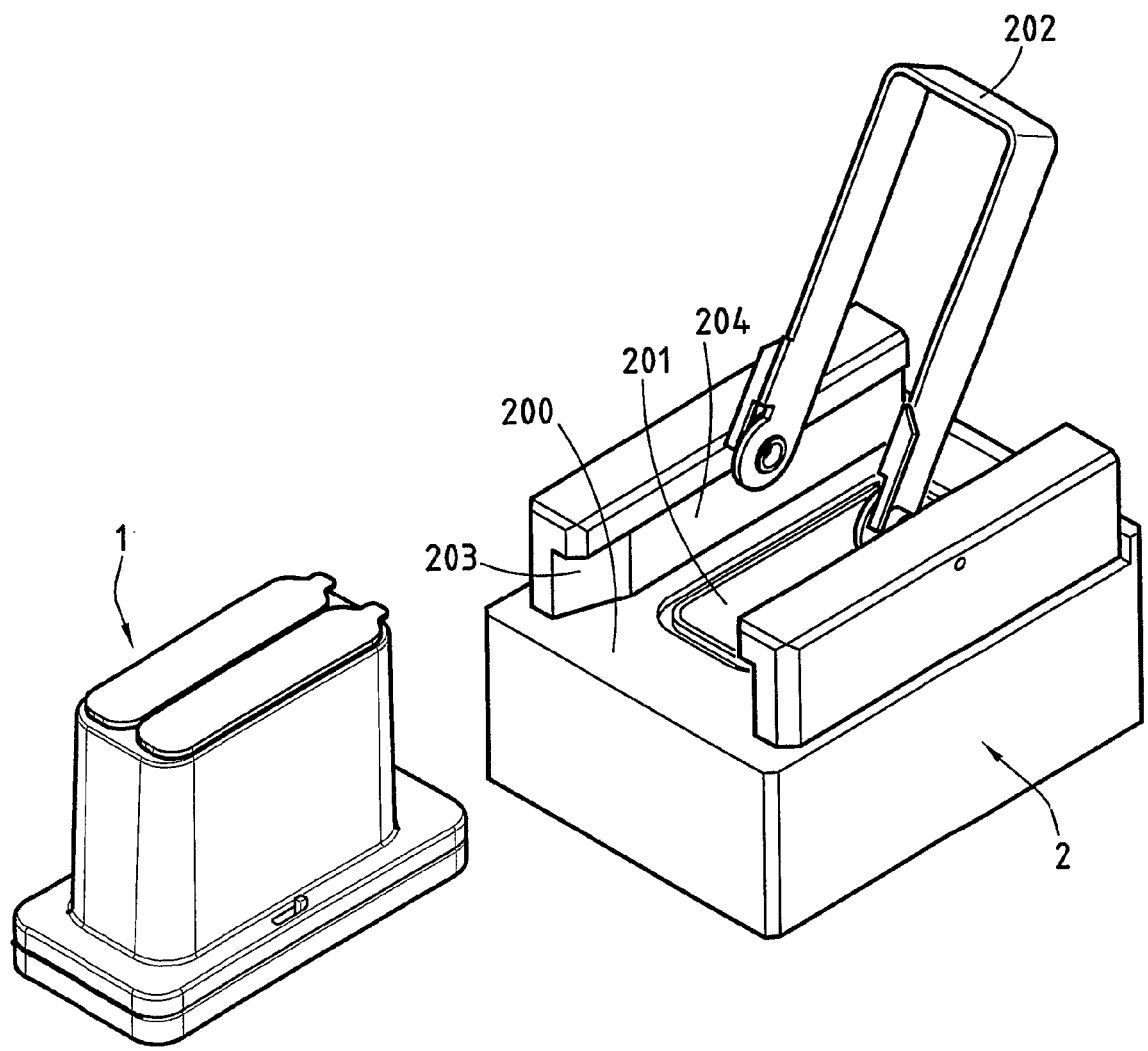
FIG. 1 is a perspective view of a filtration module associated with a filtration module support block.

The method for isolating biological particles contained in a fluid, according to the invention, consists of filtering the fluid on a filter with characteristics suited to the nature of the particles to be isolated. The biological particles may be cells, red blood cells, platelet aggregates, fibrins or tissue waste. The filtered fluid is in particular a fluid obtained from a sample of biological fluid that may have undergone prior treatment to facilitate the isolation by filtering operation. This prior operation, which will be described in more detail later, comprises in general, particularly when the particles to be isolated are cells, one or a plurality of the following operations: chemical treatment designed to pre-enrich the cell to be isolated, dilution, chemical treatment designed to facilitate separation by filtration of the cells to be isolated.

As well as these conditions for preparing samples of fluid for filtering, the inventors noted that to achieve good reliability in the process of isolating cells to be detected, it was necessary to adapt certain characteristics of the filter to the volume of fluid filtered. In particular, the filter must be divided into elementary filtration area each having a surface equal to that of a disk of diameter of between 0.6 cm and 3 cm, and preferably greater than 0.8 cm and even better between 0.8 cm and 1.5 cm. The elementary filtration areas may be in the shape of a disk, for example.

In addition, the quantity of fluid to be filtered, which must pass through each of the elementary filtration areas, must be between 1 ml and 100 ml, and preferably this volume should be between 8 ml and 15 ml.

Thus, to filter a particular sample a device must be used to define a number of elementary filtration areas on the filter in proportion to the volume of the sample to be filtered.

In general, the volume of the sample to be filtered depends on the one hand on the volume of biological fluid that could be taken initially, and on the other hand on a possible dilution which depends in particular on the nature of the biological particles to be separated. The volume taken depends in particular on the nature of the fluid taken and the age of the patient from whom the fluid is taken. A person skilled in the art knows how to determine the volumes to be taken depending on the nature of the fluid taken and on the patient from whom it is taken.

Dilution depends in particular on the number of particles per unit of volume that can be found in the fluid taken. Indeed, if filtration is to be carried out under satisfactory conditions, the number of particles to be isolated per unit of volume of fluid to be filtered should not be too great to avoid clogging the filter. Moreover, if the process is intended to detect particular rare cells mixed with a far greater number of cells, the number of cells per unit of volume should not be too small, so as to achieve a reasonable probability of finding the cells sought on the filter. A person skilled in the art also knows how to determine these dilution rates depending on the nature of the fluid in question and the type of cell sought.

The biological sample taken from a patient may, for example, be blood, urine, ascites, cephalorachidian fluid, milk or pleural extravasation; it may also be fluid from washing the neck of the uterus or any other fluid that may result from taking a biological sample from a patient.

The analysis method may also be used to search for cells in samples that have not been taken directly from patients, and for example, in samples taken in cell culture mediums made from smears or biopsies or from human or animal tissue samples or, further, in human or animal cell line culture mediums.

If the biological fluid taken is blood, the amount taken is generally between 1 ml and 20 ml, and the blood is diluted by a ratio that varies from 1 in 5 to 1 in 20 to obtain a sample of fluid for filtering which, in these conditions, is filtered over one to 20 elementary filtration areas.

For all other fluids, the samples are approximately 5 ml to 10 ml and are diluted in a ratio of between 1 in 2 and 1 in 10, or they may not be diluted. These samples are filtered over a number of elementary filtration areas which may be as many as 5 or even more, particularly if it is a 10 ml sample that has been diluted in a ratio of 1 in 10.

The cells that may be sought are in particular tumour cells, foetal cells, endothelial cells, fibroblastic cells, muscle cells, nerve cells, monocytal cells, cell strains, organ cells (hepatic, renal, etc. . . . ), precursors and haematopoietic cells. This list, which is given as an example, is not limitative.

Before filtration, the cells may be pre-enriched by treatment of the density gradient type or by lysis of cells that are of no interest, or by immunomediated methods, by positive or negative screening, by stimulating the cells sought to proliferate, etc.

This list is not limitative, and a person skilled in the art knows how to choose a pre-enrichment process suited to the nature of the cells that he or she seeks to isolate.

As well as the pre-enrichment treatment, the fluid sample containing cells may be treated by a reagent according to the nature of the cells sought, to facilitate the separation by filtration operation.

The aim of the treatment may be to lyse red blood cells and anticoagulate the blood if the biological sample contains blood, and consists, for example, of adding saponin and EDTA.

The aim of the treatment may also be to fix nucleated cells, for example by the addition of formaldehyde, if the filtration is intended to isolate fixed cells. In this case, the object of the treatment is to make enrichment possible.

If the filtration is intended to isolate non-fixed cells, the biological sample may be treated with a reagent and under conditions suitable for temporarily rendering biological membranes rigid (for example, by the addition of polysaccharide, DMSO, by cold, etc.).

A person skilled in the art knows how to choose the most suitable method, according to the nature of the cells sought.

The biological sample which may have been diluted, pre-enriched or treated with a reagent to allow filtration suited to the end sought, is then filtered through a filter made of polycarbonate or an equivalent material that has calibrated pores of a size between 1 µm and 100 µm and suited to the nature of the particles to be separated. This size is preferably between 3 µm and 25 µm, and is about 8 µm, for example, particularly if tumour cells or epithelial cells are to be isolated.

Pore density is suited to the nature of the particles to be separated. Preferably, the pore density of the filter is between $5\times10^3$ and $5\times10^6$ pores/cm$^2$ and even better between $5\times10^4$ and $5\times10^5$ pores/cm$^2$.

Filtration is performed preferably be a reduction in pressure of between 0.05 bar and 1 bar, and preferably of approximately 0.1 bar. Filtration may be assisted by a slight increase in pressure on the fluid situated above the filter. This increase in pressure must however be less than 1 bar. These conditions are particularly suited to cell separation.

The process may be used for different objectives, for example to search for rare cells in suspension in a biological fluid, so as to allow diagnosis or to purify a fluid to allow analysis in good conditions of the elements in solution.

If the process is used to search for cells and analyse them, after filtration, the filter that has been used to filter the fluid is recovered ensuring that the filtration areas are clearly identified and that a link can be made between these filtration areas and the sample that was filtered. The filter is then used to analyse the cells that it may have been possible to recover in the filtration areas.

These analysis methods, which are known per se, are for example of the following types: cytological staining (haematoxylin, eosin, etc.), immunomarking (immunohistochemistry, immunofluorescence) PNA, FISH, PRINS, PCR in situ or other molecular technique, spectrophotometry, laser microdissection followed by targeted molecular analyses on the DNA (DNA extraction, genotyping, quantitative PCR, mutation analysis, CGH (comparative genomic hybridisation)) RNA (extraction and analysis by PCR of transcripts, quantitative PCR) and proteins (protein extraction, microsequencing, etc.).

The molecular analyses may be performed on enriched cells held on the filter and transposed onto a slide by a technique similar to the Southern technique, individually micro-dissected from the filter or from the slide according to defined criteria (morphological characteristics of the cells with or without marking of different natures) and subjected to individual or pooled molecular analysis.

The cells may also be detached from the filter by washing with an appropriate buffer to extract and analyse their DNA, RNA and proteins.

The elements isolated by filtration are then examined with a microscope and analysis of the images obtained on the filter may be carried out manually or by automated means, in particular by using image analysis equipment.

The process may also be used to purify a biological fluid such as urine containing in solution the DNA, RNA or proteins that are to be analysed. The purpose of purifying the fluid is to eliminate all the biological particles present in the fluid, which could interfere with the analysis. In this case, the filters are not kept and it is the filtered fluid that is analysed.

This filtration method and the sample preparation and analysis methods may be used as stated previously in particular for the purpose of diagnosis to detect pathologies associated with the presence of particular cells possibly in extremely small quantities. In particular, the process can be used to detect cancerous cells that may have been released into a patient's blood during a surgical operation. A person skilled in the art knows what cells can be searched for to detect a particular pathology.

To ensure that these analyses are carried out under conditions of satisfactory reliability, particularly in the context of hospitals or medical analysis laboratories, it is desirable that the appliances used should provide good reproducibility and reliability of the conditions in which the analysis was performed. Accordingly, the inventors have developed devices suitable for performing these analyses in conditions of satisfactory reliability.

These devices will now be described.

To carry out the analyses in conditions of acceptable reliability, the fluids to be filtered are collected in a filtration module, preferably a single-use filtration module, referenced generally as 1 in FIG. 1 and designed to be mounted on a support block referenced generally as 2, forming part of the filtration machine (which is not illustrated in its entirety in the figure).

The filtration module 1 is placed on the support block to perform the filtration. When filtration has finished, the filtration module 1 is removed from the support block 2 and the filter contained in the filtration module is removed so that the analyses can be performed as will be explained later.

Figure 2:
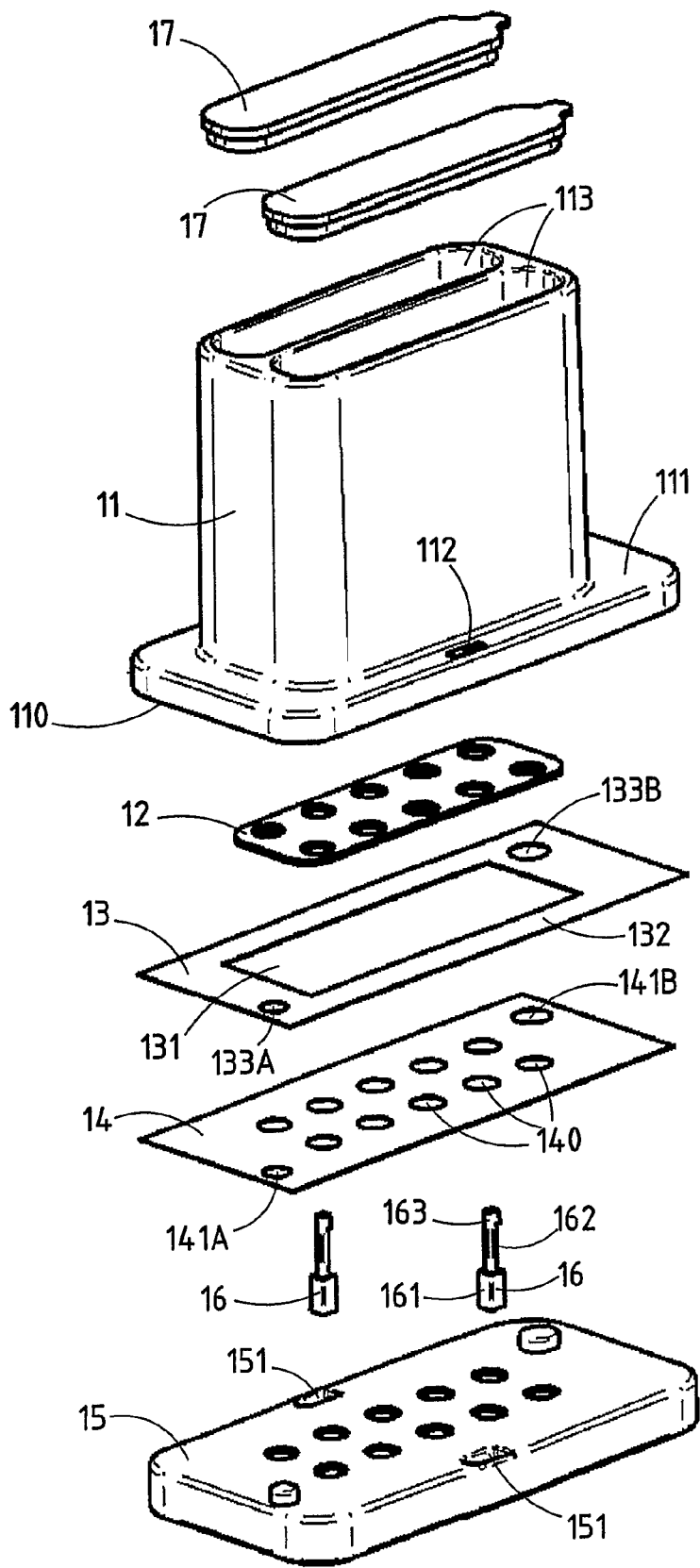
FIG. 2 is an exploded perspective view of a filtration module.

The filtration module 1, illustrated in exploded form in FIG. 2, consists of a stack comprising, from top to bottom, a chamber block 11, a grooved joint 12, a filter 13, a plate joint 14 and a filter support drawer 15.

The filter 13 is laid flat against the lower face 110 of the chamber block 11 by means of the filter support drawer 15, the seal between the filter 13 and the chamber block 11 being provided by the grooved joint 12, and the seal between the filter 13 and the filter support drawer 15 being provided by the plate joint 14.

When the assembly is fitted together, the filter support drawer is held in position against the chamber block 11 by means of two assembly pins 16 which pass through holes 151 in the filter support drawer and hook into holes 112 provided in a lower rim 111 of the chamber block 11, extending outwards.

The chamber block 11, made of plastics material, comprises a body 114 divided into two compartments 113 open at their upper portion 115 and closed at their lower portion by a base 116 comprising a plurality of circular openings 117 with a diameter of between 0.6 cm and 2 cm. The base also comprises a rim 111 forming a small collar in which openings 112 designed to receive the hooks of the assembly pins 16 are provided on the two side portions of the chamber block. The compartments 113 may be closed at their upper portion by removable stoppers 17. The fillet radii of the base and walls of each compartment are rounded so as not to create an area where particles to be filtered can be trapped.

Figure 3:
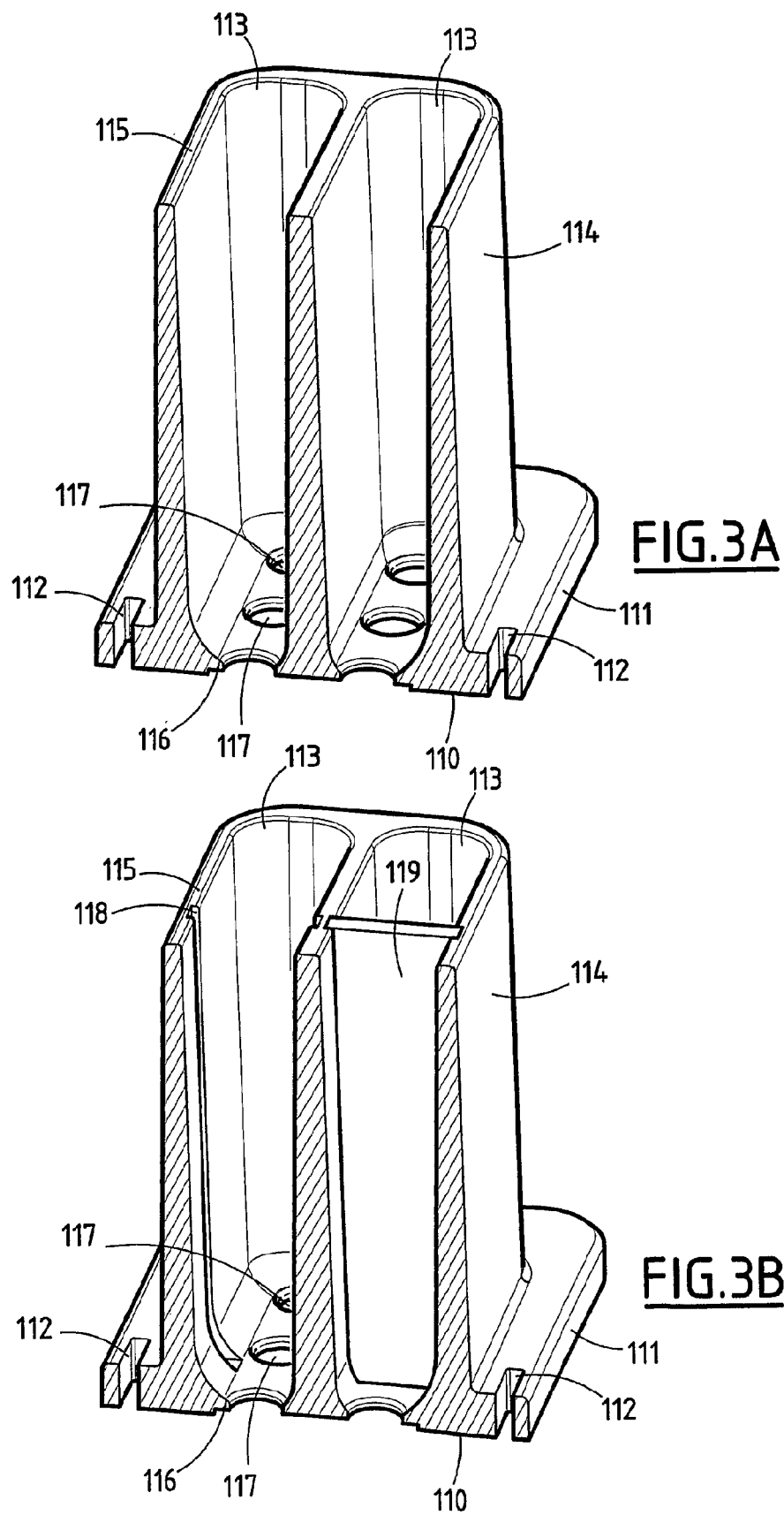
FIGS. 3A and 3B are two views in cross-section of a chamber block of a filtration module.
Figure 4:
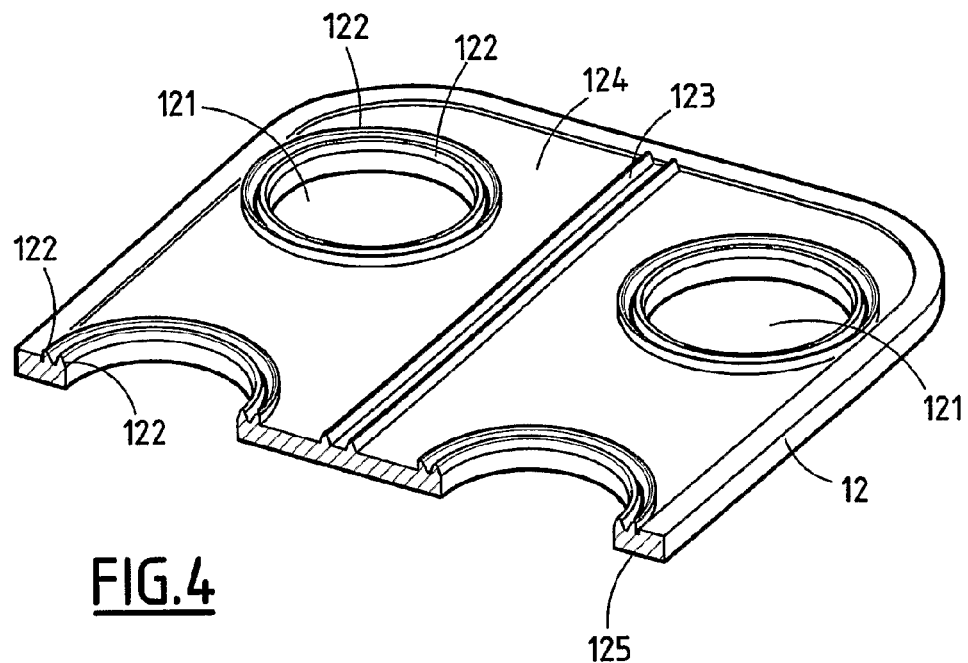
FIG. 4 is a perspective view with cross-section of a grooved sealing joint.

As can be seen in FIG. 3B, the compartments 113 may comprise vertical grooves 118 designed to receive separation slides 119 allowing the compartments 113 to be divided into part compartments of smaller volume. The grooves 118 are arranged such that any separation slides 119 are always arranged between two circular openings 117.

To ensure appropriate filtration, the volume of the compartments is in proportion to the number of circular openings 117, such that the total volume of the compartment or more precisely the maximum quantity of fluid that the compartment can receive is between 0.14 ml/cm$^2$ and 40 ml/cm$^2$ multiplied by the sum of the surfaces of the openings comprised in the base of the compartment. In particular, the height of the compartment and the cross-section of the base are such that not only are these conditions respected for a complete compartment but also such that they are respected for any part compartment delimited by means of one or a plurality of removable sealed separation walls 119. In particular, if an opening 117 is isolated by two removable walls 119, or by one removable wall 119 and by the wall of the compartment, so that it only comprises one opening 117 in the base, the volume situated above the opening 117 is suitable for receiving a maximum of 20 ml of fluid for filtering. As an example, each compartment may have a volume of 110 ml and comprise 5 openings in the base.

In a variant illustrated in FIG. 8, the chamber block 11 comprises a compartment 113, comprising five elementary filtration areas, a compartment 113A comprising one elementary filtration area and two compartments 113B comprising two elementary filtration areas. Each compartment comprises a removable stopper 17, 17A, 17B. It will be noted that with this arrangement, it is possible to choose the number of elementary filtration area used from between 1 and 10.

On its lower face 110, the chamber block comprises two holes of different diameter (not visible on the figure) arranged diagonally, designed to cooperate with studs 153A and 153B of the filter support drawer 15, to ensure precise positioning and location of the position of the filter in relation to the base of the chamber block.

The grooved joint 12 arranged just beneath the chamber block is made of moulded silicon and comprises a plurality of holes 121 designed to face the openings 117 provided in the base of the chamber block, these holes 121 being surrounded by circular lips 122, and preferably by two circular lips, to provide a good seal. The joint may also comprise longitudinal grooves 123 for separating a first series of holes from a second series of holes, to provide separation between the holes opposite a first compartment and the holes opposite the second compartment of the chamber block. The function of this joint is to provide a perfect seal between each of the holes so that the fluid passing through a hole cannot be mixed with the fluid passing through another hole, which allows simultaneous filtration of two different fluids. The projecting lips 122, and possibly 123, are arranged on the face 124 of the joint designed to cooperate with the lower portion of the chamber block 11. The second face 125 of the joint, designed to cooperate with the filter 13, is flat.

The filter 13, which forms a badge of generally rectangular shape and which is flat, comprises a central filtration area 131 consisting of a membrane made of microporous polycarbonate, about 100 μm thick and of a porosity appropriate to the process. This central portion is fixed using biological glue on a PVC frame 132 that can be used to grasp the badge and on which reference inscriptions can be made. The frame 132 comprises means for positioning and locating the orientation of the badge consisting of two holes 133A and 133B arranged diagonally on the badge and having different diameters designed to cooperate with the studs 153A and 153B of the filter support. With this arrangement of location holes 133A and 133B, only one orientation is possible to arrange the badge on a support comprising complementary location studs for the holes 133A and 133B. This allows the orientation of the badge to be located very exactly on the one hand when it is arranged in the separation module and on the other hand when it is arranged on an analysis appliance such as equipment for staining or reading under a microscope.

In a variant illustrated in FIG. 9, the badge comprises two central filtration areas 131A, 131B parallel to each other and which may comprise membranes of different porosity.

The plate joint 14 is a flat plate joint made of silicon comprising circular openings 140 corresponding to openings 121 in the grooved joint and to openings 117 provided in the base of the chamber block. It also comprises holes 141A and 141B of different diameter corresponding to the holes 133A and 133B of the filter.

The filter support drawer 15 is a plate made of injected plastics material comprising an upper face 150 designed to grip the filter and joints assembly against the lower face 110 of the chamber block 11. This filter support plate comprises a series of holes 152 designed to face the corresponding holes 140 of the plate joint, 121 of the grooved joint and 117 of the chamber block.

The upper face 150 of the filter support drawer also comprises studs 153A and 153B designed to cooperate with the location holes 133A and 133B of the filter badge 13, with the corresponding holes 141A and 141B of the plate joint 14 and with the centring holes provided on the lower face 110 of the chamber block.

Figure 5A:
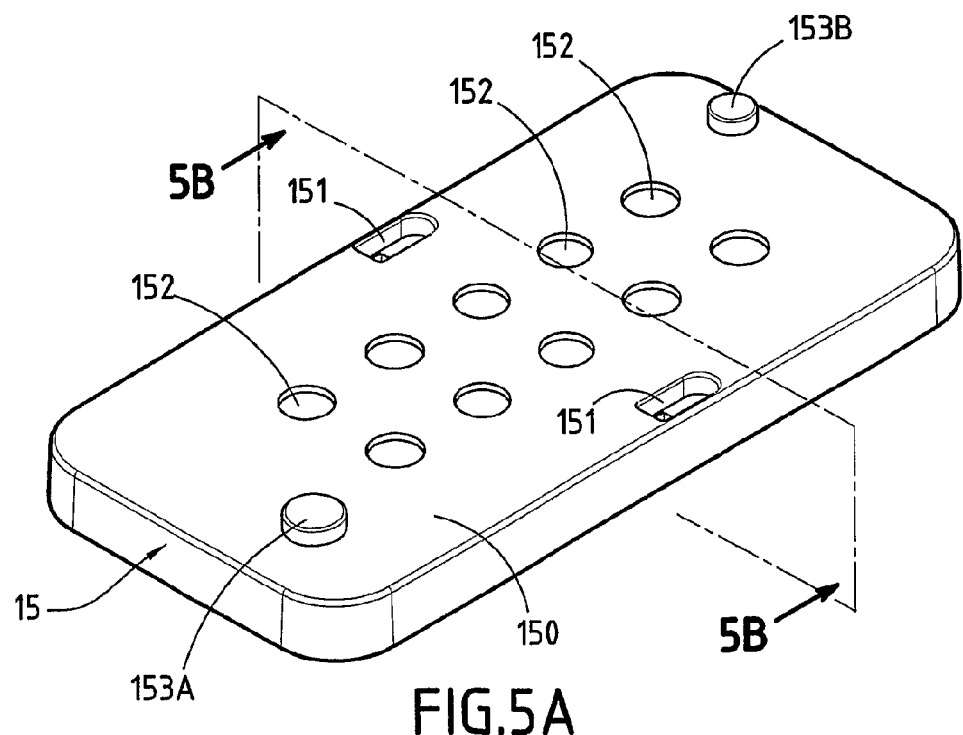
FIGS. 5A and 5B are perspective views, in particular with a cross section, of a filter support drawer.
Figure 5B:
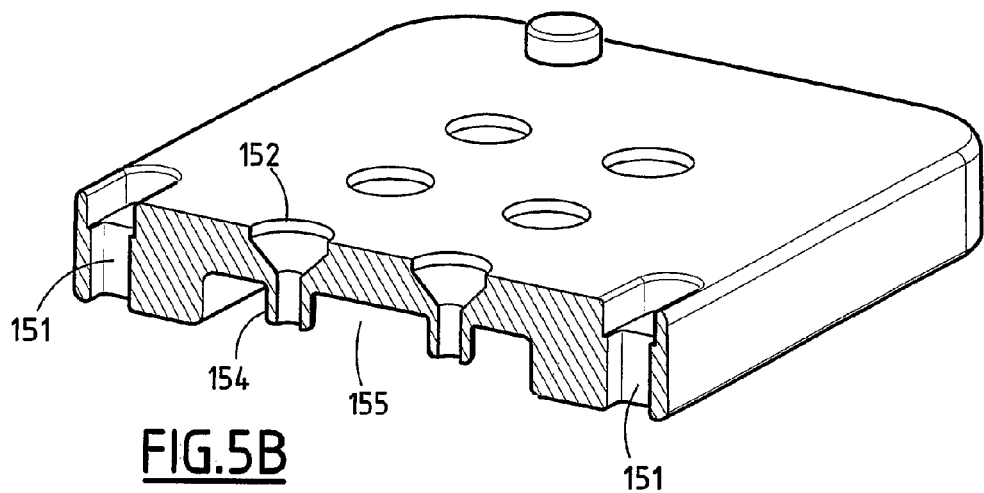
Figure 6A:
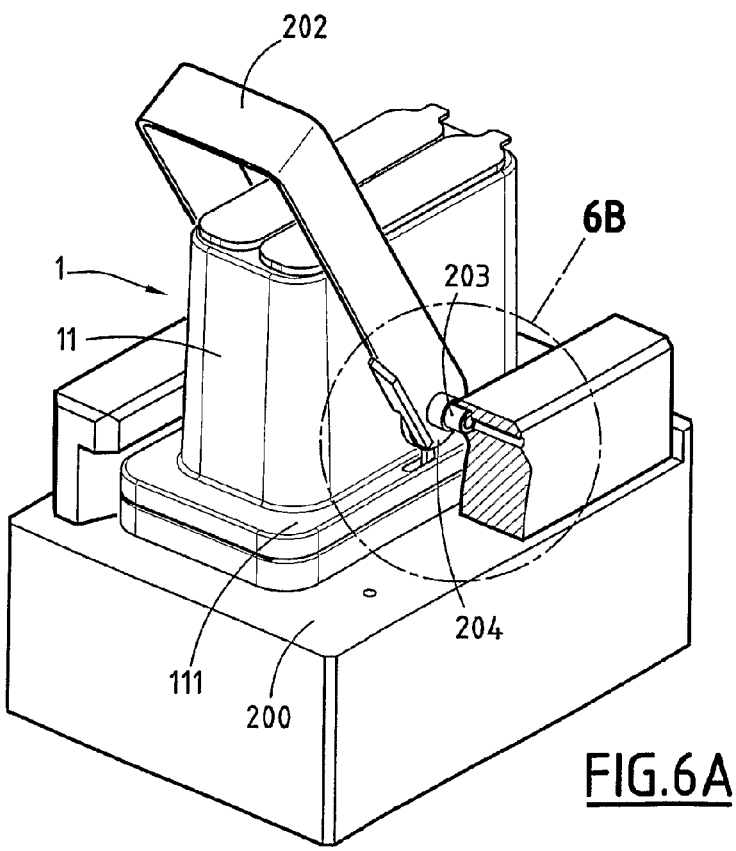
FIG. 6A is a perspective view of a filtration module arranged on a support block.
Figure 6B:
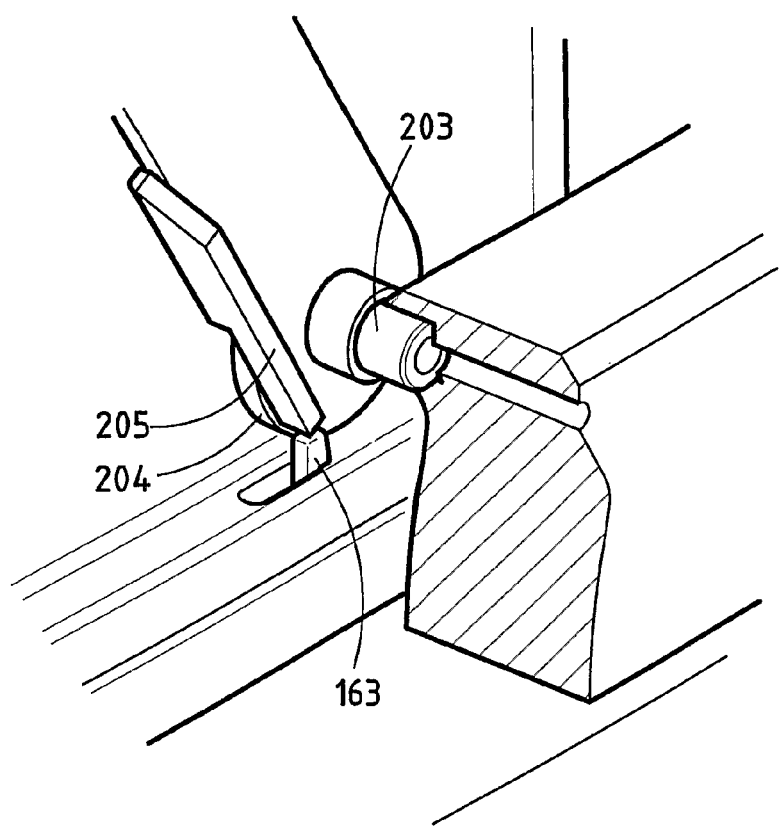
FIG. 6B is an enlarged perspective view of means for gripping the base of a filtration module arranged on a support block of the filtration module.

As can be seen in FIG. 5B, the holes 152 designed to allow the filtered fluid to pass through comprise an upper portion in the form of a funnel which is extended by small tubes 154 projecting on the lower face 155 of the filter support drawer 15. The function of the small tubes 154 projecting in relation to the lower face 155 of the filter support drawer is to ensure that the fluid flows properly after filtration so that no drops are formed that could moisten the lower face of the filter support. It will be noted that the diameter of the upper portion of the holes 152, like the diameter of the holes 140 of the plate joint and 151 of the grooved joint, are substantially equal to the diameter of the holes 117 provided in the base of the chamber block, in order to delimit elementary filtration areas of corresponding diameter on the filter. The filter support drawer 15 also comprises holes 151 on its two side edges designed to receive the assembly pins 16. These holes are of a suitable shape to allow the introduction of the assembly pins and lock the unit in position when assembling the filtration module unit.

The assembly pins 16 each comprise a head 161 surmounted by a stem 162, of smaller diameter, the end of which forms a hook 163. The length of the assembly pin is suitable to allow the stack made up of the filter support drawer, the joints and the filter to be locked when it is laid flat against the chamber block. Thus, an assembly pin is of sufficient length to ensure that, when it is introduced into a hole 151 of the filter support drawer, it can penetrate into the hole 112 of the lower rim of the chamber block 11, such that the hook 163 situated at the end of the assembly pin can hook on the upper surface of the rim 111 of the chamber block, the head 161 of the assembly pin 16 cooperating with the lower face of the filter support drawer 15 so as to maintain the filter support drawer locked against the base of the chamber block 11.

The filtration module as just described is designed to be arranged on a support block 2 of the filtration module, which comprises on the one hand a support face 200 comprising a central opening 201 designed to face all the openings on the lower face of a filtration block, on the other hand a lever 202 pivoting about a pin 203 designed to manoeuvre two cams 204 (only one of which can be seen in the figure) for gripping the lower portion of the filtration module tightly against the surface 200 of the support block, and thereby to grip the chamber block 11 tightly against the filter support drawer 15 during filtration operations.

In a preferred variant, illustrated in FIG. 8, the lower rim 111 of the chamber block and, possibly the filter support drawer 15, comprise at one end, an enlarged portion 114 designed to cooperate with an enlarged portion 203 of the runner 204 of the support block 2 designed to receive the base of the filtration module. This arrangement allows an orientation to be imposed on the filtration module in relation to the support block.

When the filtration module 1 is arranged on the support block 2, the cams are facing the rim 111 of the chamber block 11, such that when the lever is in the open position, the cams leave room for the rim 111 to slide on the upper face 200 of the support block, and when the lever is in the gripping position, the cams rest firmly on the rim 111 of the chamber block 11, so as to grip the unit formed by the filtration block, the filter, the filter support and the associated joints, against the face 200 of the filtration module support.

Figure 7:
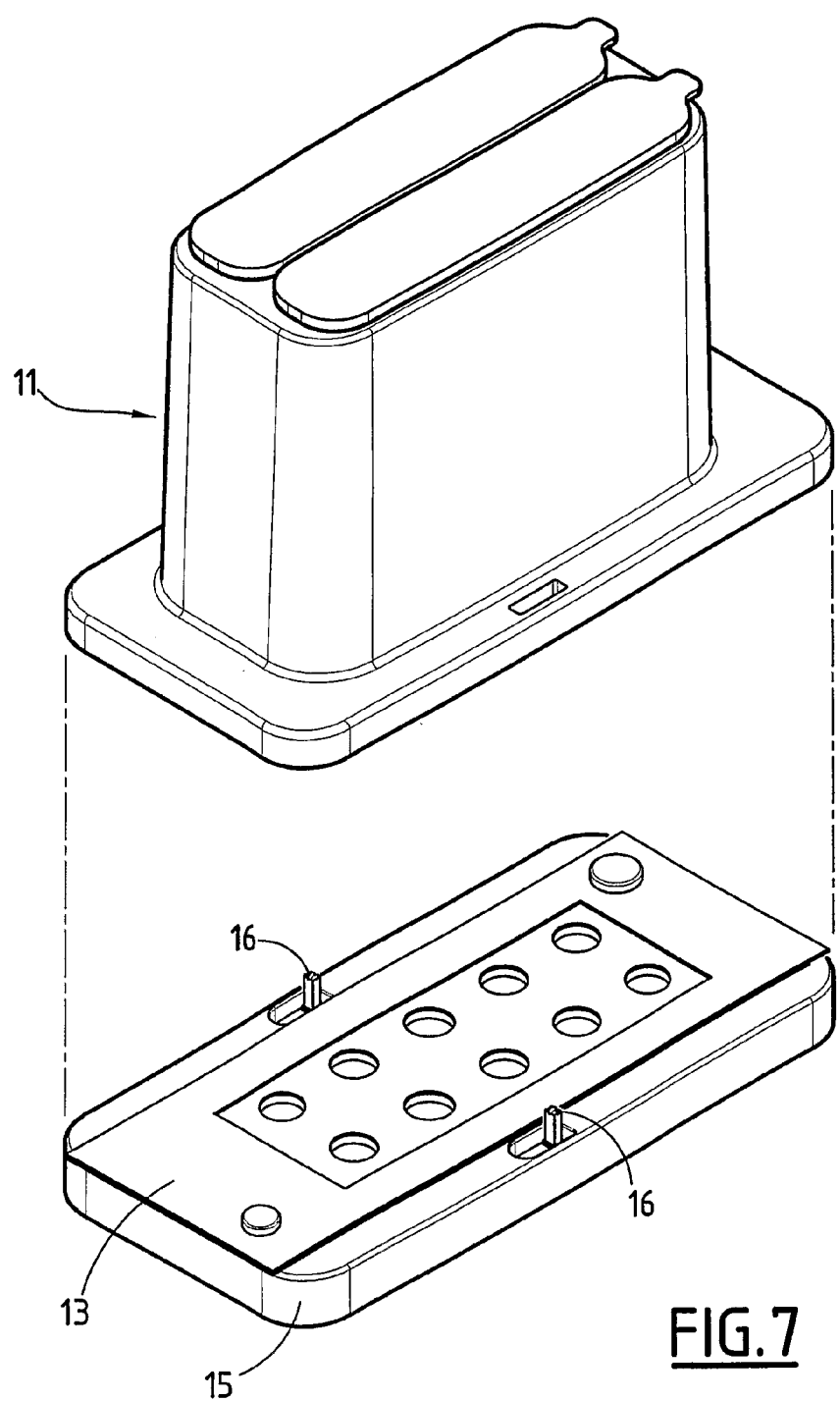
FIG. 7 is a separated perspective view of a filtration module after use, in which the chamber block is separated from the filter support drawer comprising a filter.

Moreover, each cam comprises a vane 205 projecting outwards which, when the rim of the filtration module is tightened, cooperates with the end of the corresponding assembly pin 16, in order to break the hook so that, when full tightening has been achieved, the hook of the assembly pin is broken. Because of this arrangement, when the filtration module is tightened against the support block 2 by means of the cam, the unit is held together tightly, while, after loosening the cam, since the head of the hook has been broken, the filter support block and the chamber block are no longer integral with each other as illustrated in FIG. 7. This allows the filter to be removed and, at the same time, renders the filtration module unusable for another analysis. The filtration module is therefore a single-use module.

A block that does not comprise breakable hooks can also be used. Such a block can then be used repeatedly, which is less reliable than a single use, but may nevertheless have attractions in some cases.

Before any use, the filtration module is closed using the upper stoppers and sterilised. If a sample is to be filtered for analysis purposes, a sterilised filtration module is taken and arranged on a support block of a filtration machine. Using the tightening lever, the filtration module is locked on the filtration machine ensuring that the filter support plate is gripped firmly against the base of the chamber block. By doing this, if it is a single-use module, the ends of the assembly pins comprising hooks are broken. At least one of the compartments into which the fluid to be filtered is introduced is then opened so that, in each compartment, the ratio of the amount of fluid contained to the sum of the surfaces of the openings of the base of the compartment is between 0.14 and 40 ml/cm$^2$. Filtration is then carried out. Once the filtration is performed, the system is unlocked by raising the tightening lever, and the filtration module is removed.

On this filtration module, the lower portion made up of the filter support plate is not integral with the chamber block. The unit is therefore separated and the filter is then removed and arranged on the platen of an observation microscope, possibly after having made a number of preparations using reagents to allow convenient observation of the cells that may have been trapped by the filter.

The rest of the device, that is to say the chamber, the filter support and the joint, are then thrown in the dustbin so that they cannot be reused. This single-use device has the advantage of providing good analysis security. In fact, the same device is used only to analyse a single sample, which avoids all risk of a sample being contaminated by earlier samples that may have been analysed using the same device. Moreover, because of the particular geometric characteristics of both the holes arranged in the base of the chamber and of the chamber sizes, the amounts of fluid filtered by the device are suitable to ensure that the amounts filtered on each of the elementary filtration areas of the filter comply with the conditions imposed by the process to achieve reliable results.

The invention claimed is:

1. Filtration module configured to separate cells on the basis of their size in small quantities from cells in greater number in a biological fluid, said filtration module comprising:
   a chamber block comprising at least one compartment closed at its lower portion by a base comprising at least one opening;
   a filter support drawer comprising at least one hole, each hole being arranged facing an opening in the chamber block, wherein the holes in the filter support drawer comprise an upper portion in the form of a funnel which is extended by small tubes projecting on the lower face of the filter support drawer;
   a filter gripped between the lower face of the chamber block and the support drawer,
   wherein the dimensions of each opening in the base of the chamber block and the dimensions of each hole in the filter support drawer are such that each pair made up of an opening in the base of the chamber block and the associated hole in the filter support drawer, define an elementary filtration area of limited surface, in that the useful volume of each compartment is proportional to the number of elementary filtration areas situated in the base of the compartment and in that the surface of each elementary filtration area is equal to that of a disk having a diameter of between 0.6 cm and 3 cm, and in that the ratio of the useful volume of each compartment to the sum of the surfaces of the elementary filtration areas of the compartment is between 0.14 ml/cm$^2$ and 40 ml/cm$^2$.

2. Filtration module according to claim 1, wherein the dimensions of at least one opening in the base of the chamber block and the dimensions of a corresponding hole in the filter support drawer are such that the surface of the corresponding elementary filtration area is equal to that of a disk 0.8 cm in diameter.

3. Filtration module according to claim 1, wherein at least one compartment may be divided into part compartments by at least one removable separation wall, such that at least one part compartment comprises in its base at least one opening and in that the ratio of the volume of said part compartment to the sum of the surfaces of the openings comprised in the base of the part compartment is between 0.14 ml/cm$^2$ and 40 ml/cm$^2$.

4. Filtration module according to claim 1, wherein it also comprises a grooved sealing joint arranged between the base of the chamber block and the filter, comprising an aperture corresponding to one opening in the base of the chamber block, said aperture being surrounded by at least one projecting lip.

5. Filtration module according to claim 1, wherein it also comprises a plate joint between the filter and the filter support, comprising at least one opening hole facing a hole in the filter support.

6. Filtration module according to claim 1, wherein the filter forms a badge, the central portion of which comprises at least one porous area and the periphery of which forms a frame comprising means for indexing its position on the filter support.

7. Filtration module according to claim 6, wherein the indexation means are at least two holes of different diameter designed to cooperate with studs of corresponding diameter provided on the filter support.

8. Filtration module according to claim 1, wherein at least a central porous portion of the filter comprises between $3 \times 10^3$ and $5 \times 10^6$ pores per cm$^2$, said pores having a size of between 3 μm and 100 μm.

9. Filtration module according to claim 1, wherein it also comprises at least one stopper for closing the upper opening of a compartment.

10. Filtration module according to claim 1, wherein the chamber block comprises, at its lower portion, a rim extending outwards and cooperating with at least one assembly pin allowing the filter to be gripped between the filter support drawer and the chamber block, the assembly pin comprising a breakable end extending above the rim of the chamber block.

11. Filtration module according to claim 1, wherein all its parts are made of materials suited to a sterilisation operation or designed to render them free from RNases, DNases or proteinases.

12. Filtration module according to claim 1, wherein it comprises means designed to cooperate with complementary means on a support block comprising at least one cam that can move between an open position and a gripping position, designed to put pressure on the filter between the filter support drawer and the chamber block, so as to impose the orientation of the filtration module in relation to the support block.

13. Filtration module according to claim 1, wherein at least a central porous portion of the filter comprises between $3 \times 10^3$ and $5 \times 10^6$ pores per cm$^2$, said pores having a size of between 5 μm and 25 μm.

14. Filtration module according to claim 1, wherein said biological fluid is blood.

15. Filtration module according to claim 1, wherein the filter used having calibrated pores of between 5 μm and 25 μm.

16. A separation device comprising a support block and a filtration module according to claim 1, wherein said support block comprises at least one cam that can move between an open position and a gripping position, designed to put pressure on the filter between the filter support drawer and the chamber block.

17. The separation device according to claim 16, wherein at least one cam is designed so that, if the filtration module comprises at least one fixing pin one end of which is breakable, the end of at least one fixing pin is cut when pressure is applied to the filter by at least one cam.

18. The separation device according to claim 16, wherein the support block comprises a means designed to cooperate with means on the filtration module, so as to index the orientation of the filtration module in relation to the support block.

* * * * *